(12) United States Patent
Kang et al.

(10) Patent No.: US 8,002,543 B2
(45) Date of Patent: Aug. 23, 2011

(54) ORTHODONTIC BRACKET, BRACKET POSITIONING JIG, AND SYSTEM FOR REVISING A SET OF TEETH

(75) Inventors: Seok Jin Kang, Gyeonggi-do (KR); Chang Ok Oh, Seoul (KR); Stephen Chu, Carrollton, TX (US)

(73) Assignee: Orapix Co., Ltd., Seoul (KR)

( * ) Notice: Subject to any disclaimer, the term of this patent is extended or adjusted under 35 U.S.C. 154(b) by 206 days.

(21) Appl. No.: 12/262,719

(22) Filed: Oct. 31, 2008

(65) Prior Publication Data
US 2009/0136890 A1 May 28, 2009

(30) Foreign Application Priority Data

May 4, 2006 (KR) .................. 10-2006-0040734
May 4, 2006 (KR) .................. 10-2006-0040735

(51) Int. Cl.
*A61C 3/00* (2006.01)
(52) U.S. Cl. ........................................................... 433/3
(58) Field of Classification Search .................. 433/2, 3, 433/8–17, 24
See application file for complete search history.

(56) References Cited

U.S. PATENT DOCUMENTS

| | | | | |
|---|---|---|---|---|
| 3,896,548 | A * | 7/1975 | Zahn ................................ | 433/74 |
| 5,429,499 | A * | 7/1995 | Sernetz ............................. | 433/8 |
| 6,123,544 | A * | 9/2000 | Cleary ............................. | 433/24 |
| 6,887,075 | B2 * | 5/2005 | Kawaguchi et al. ............. | 433/17 |
| 2003/0224310 | A1 * | 12/2003 | Andreiko ........................... | 433/3 |
| 2004/0005523 | A1 * | 1/2004 | Kapit ................................ | 433/3 |

\* cited by examiner

*Primary Examiner* — John J Wilson
(74) *Attorney, Agent, or Firm* — Rosenberg, Klein & Lee

(57) ABSTRACT

A system for revising a set of teeth including a bracket for revising a set of teeth and a bracket positioning jig is provided. The bracket positioning jig includes a cap at the lower portion of which a groove contacting tooth is formed, and which has a throughhole to lengthy direction on the upper portion of a cap body, and a connector one side of which has a fixed protrusion which is detachably inserted into and fixed to the throughhole of the cap, and the other side of which is bent toward the lower end of the body and has a coupler which is combined on a slot of an orthodontics treatment bracket for revising a set of teeth. An individual prescription value which is the most appropriate for an individual patient is given to the bracket positioning jig on a computer program to thus manufacture a desired jig, so that a non-prescription bracket as well as a bracket having a given prescription value can be used.

7 Claims, 14 Drawing Sheets

[Figure 1A]
PRIOR ART
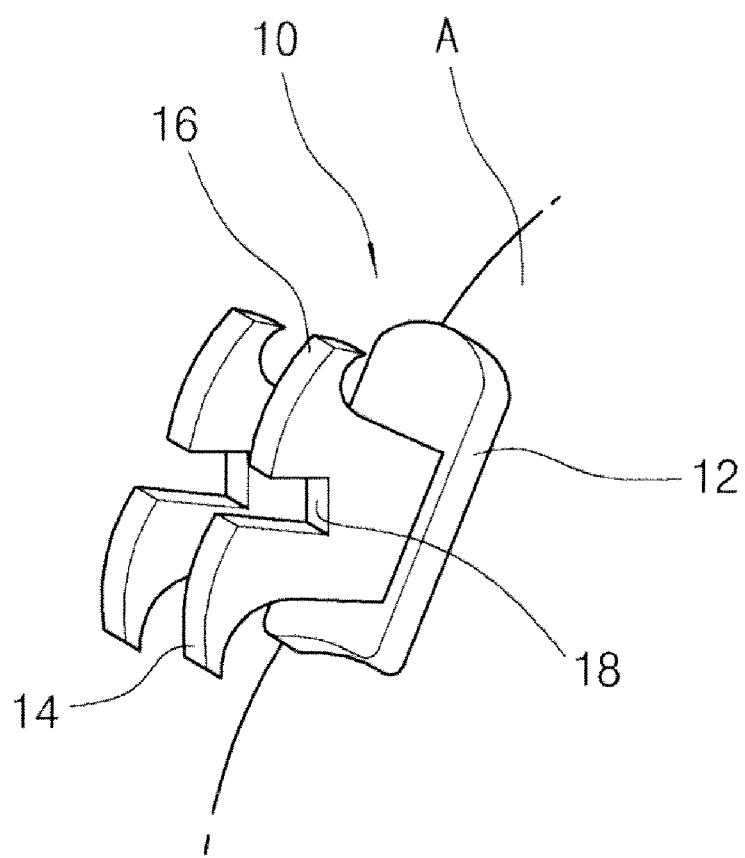

【Figure 1B】
PRIOR ART
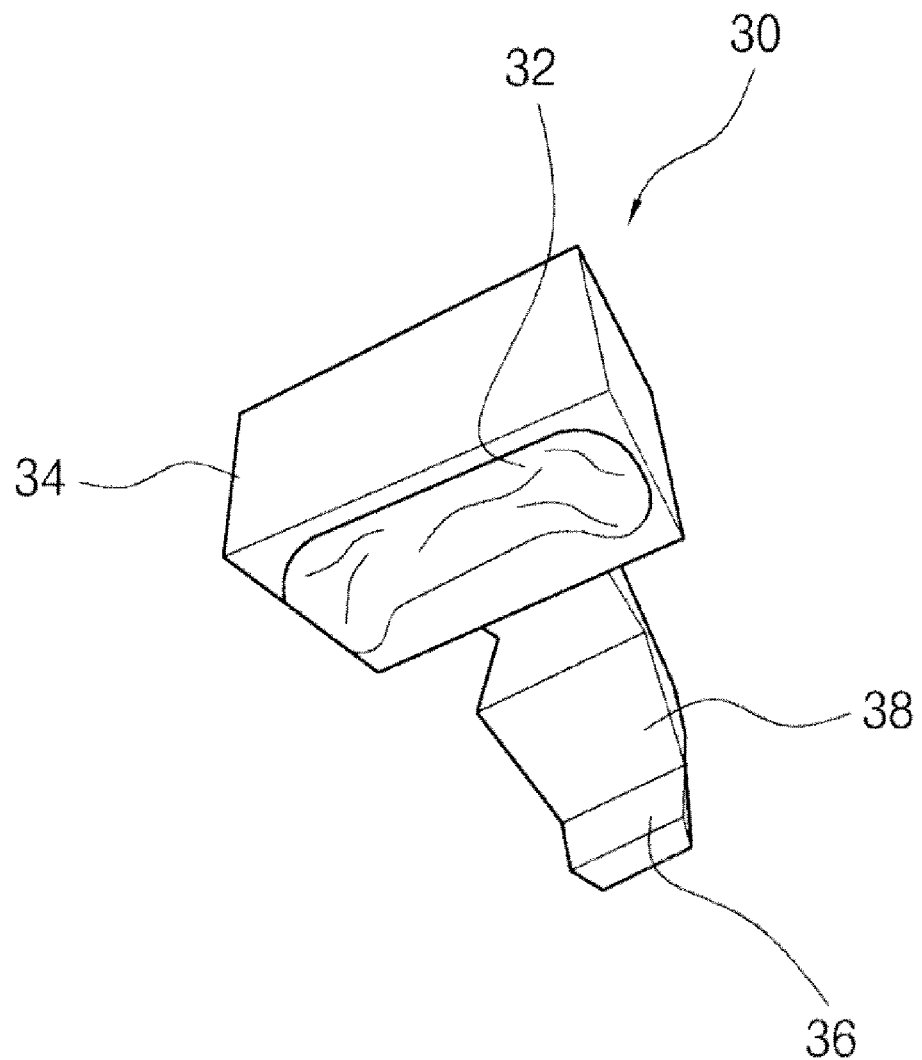

[Figure 2]
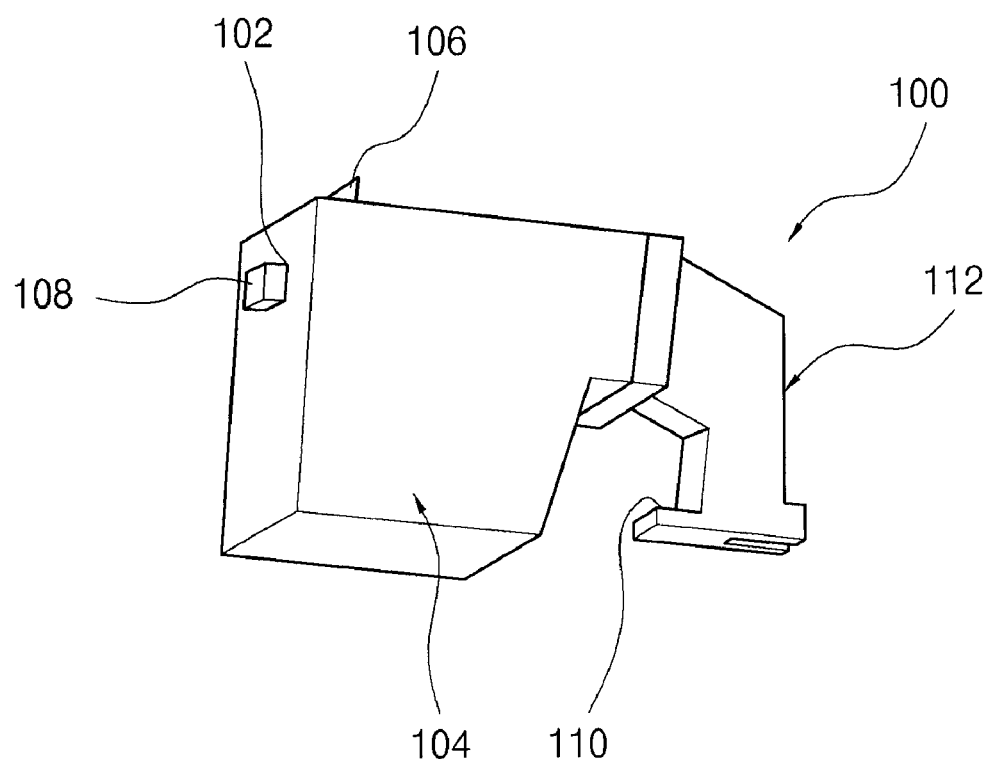

[Figure 3]
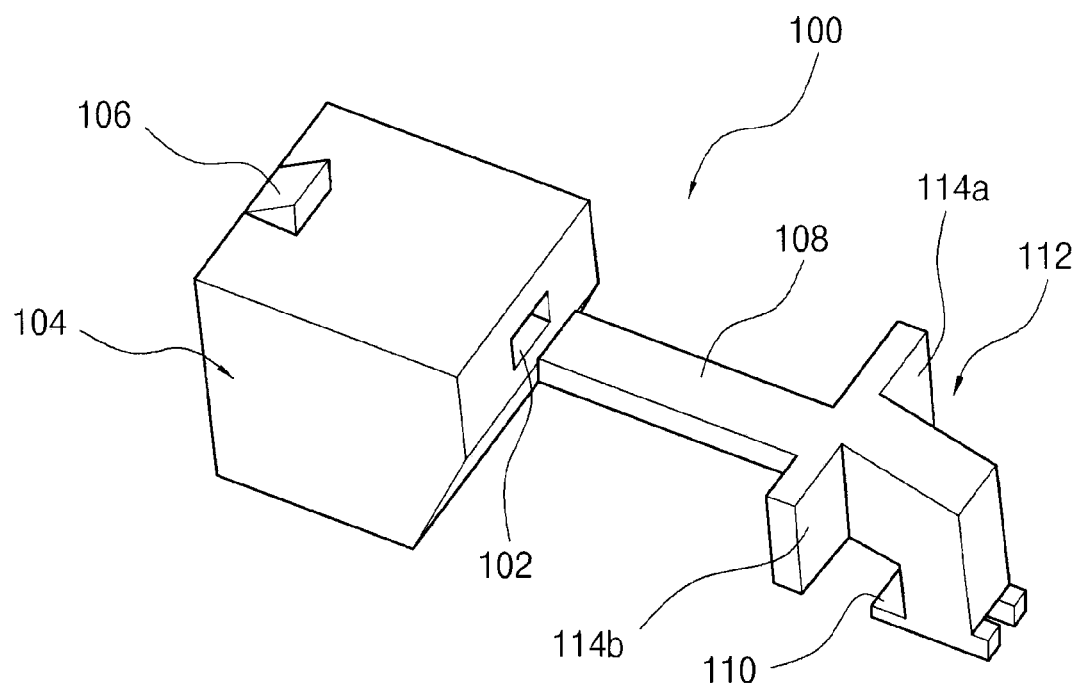

【Figure 4A】
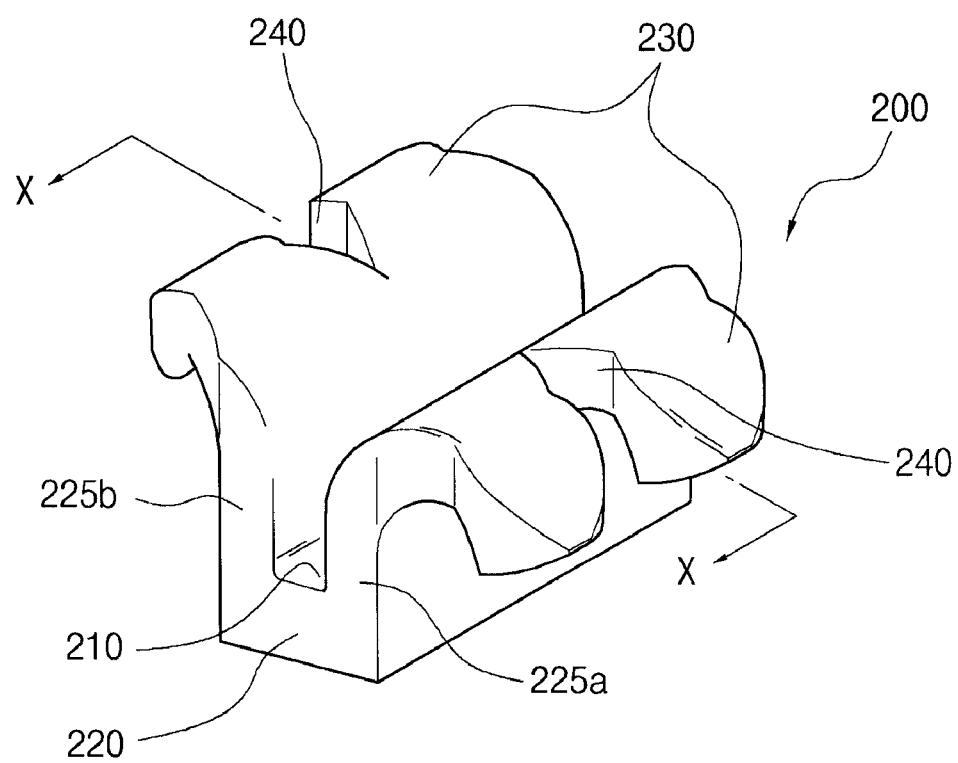

【Figure 4B】
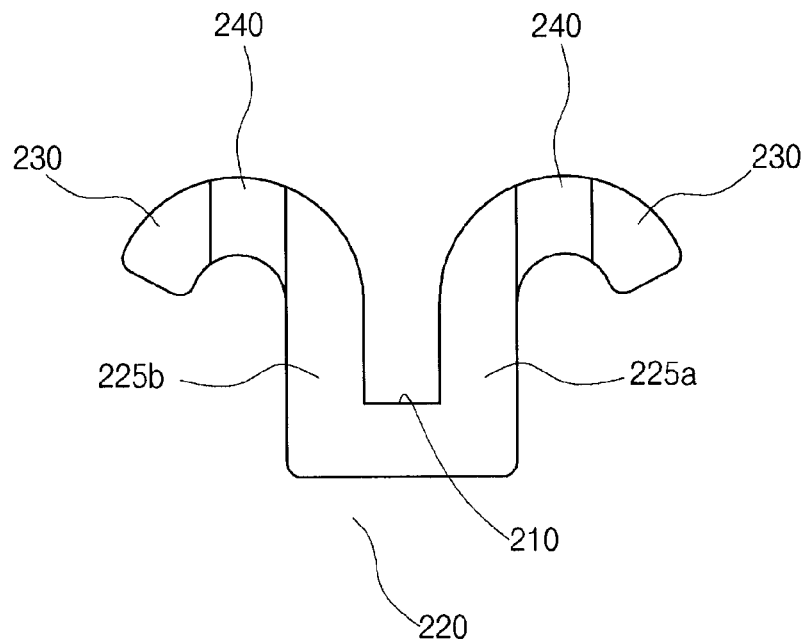
【Figure 4C】
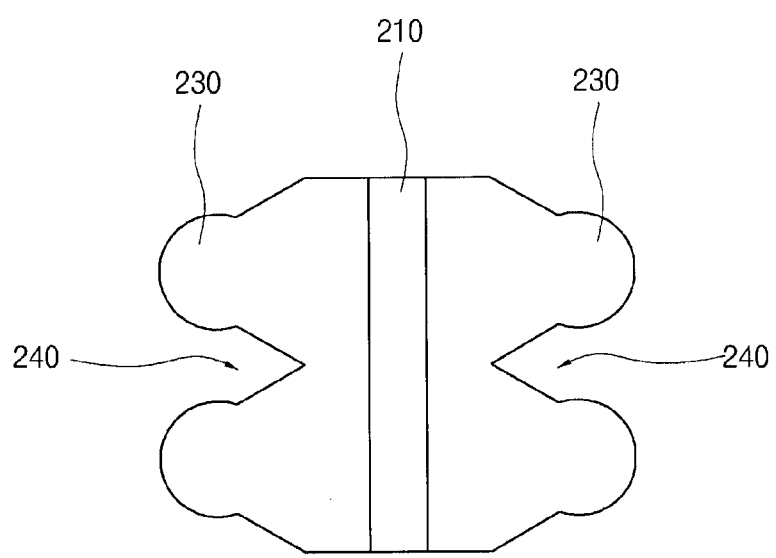

[Figure 5]
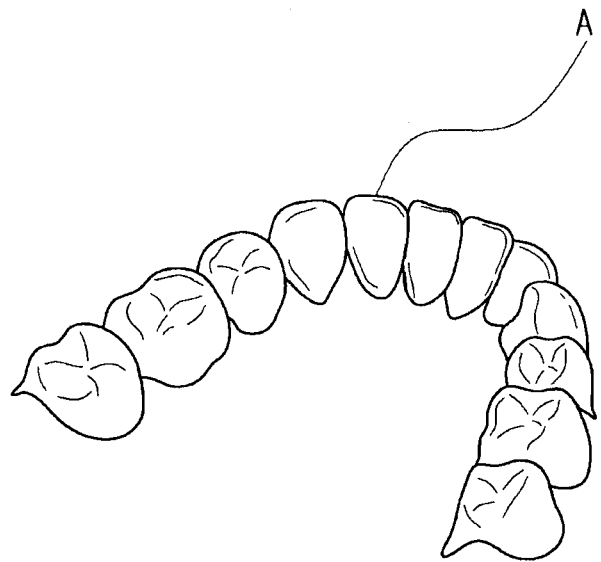
[Figure 6]
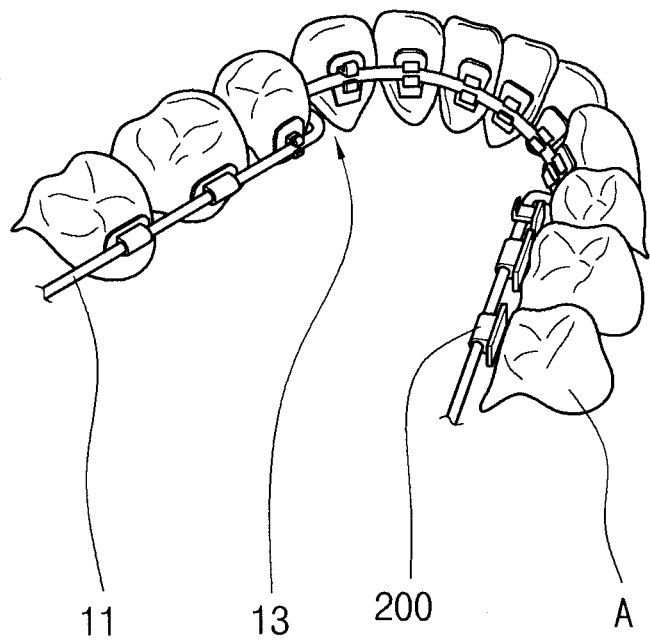
11   13   200   A

【Figure 7】
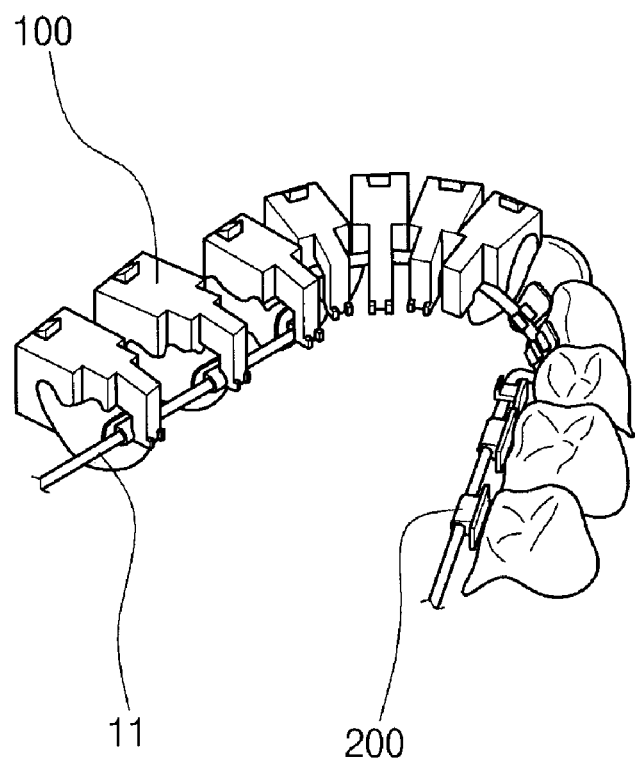

[Figure 8]
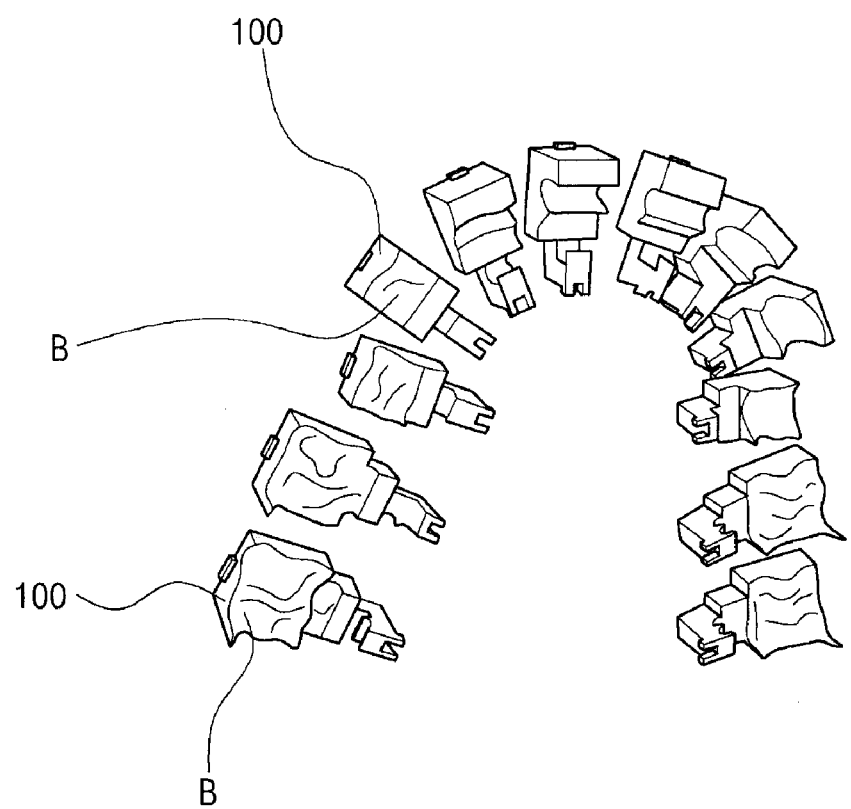

[Figure 9]
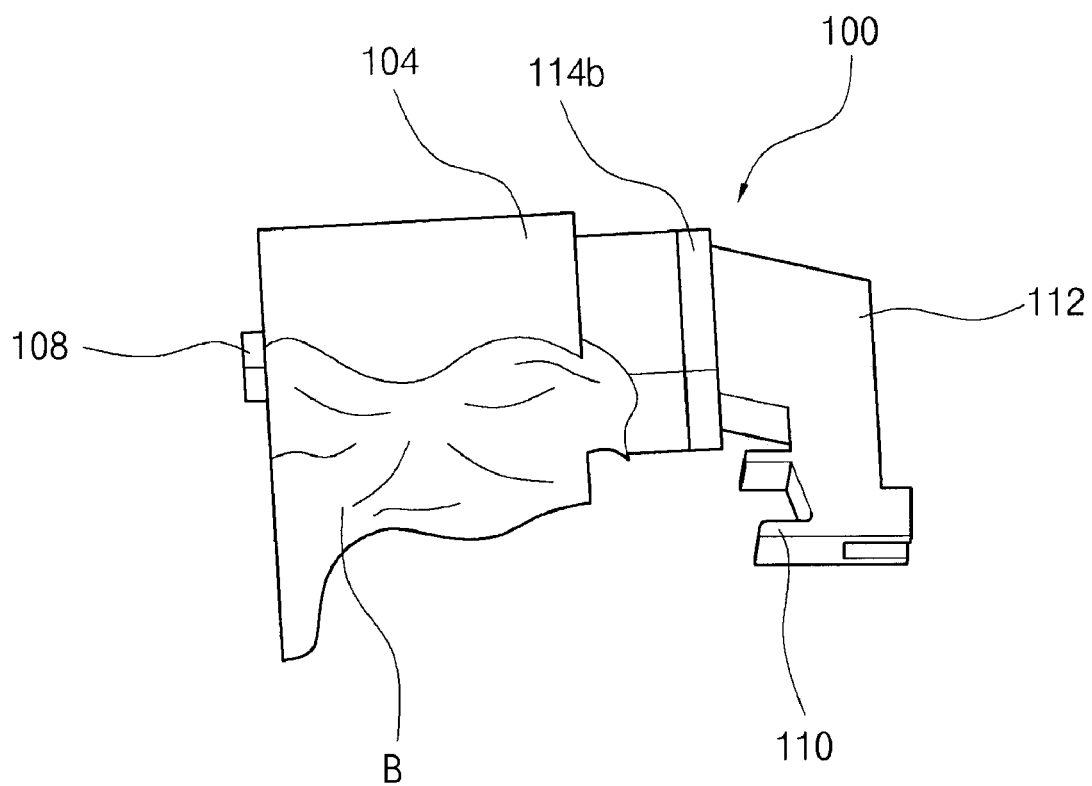

【Figure 10】
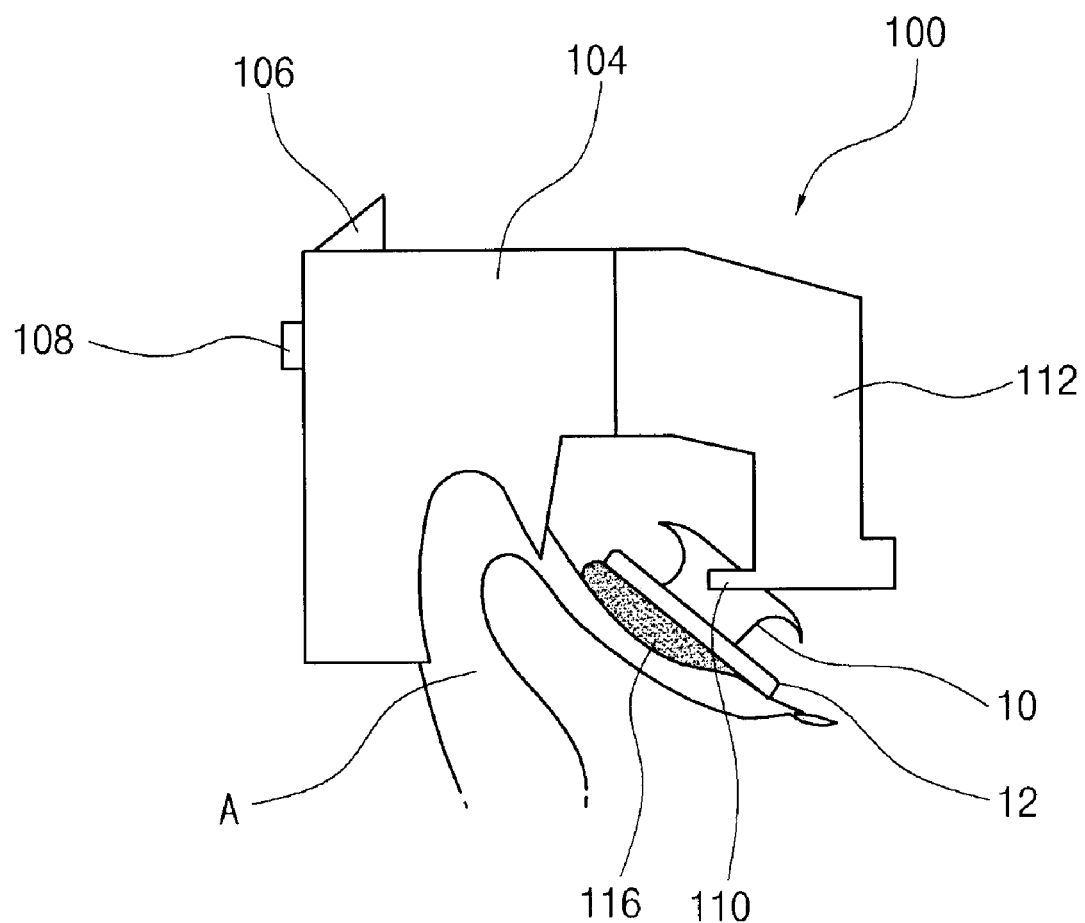

[Figure 11]
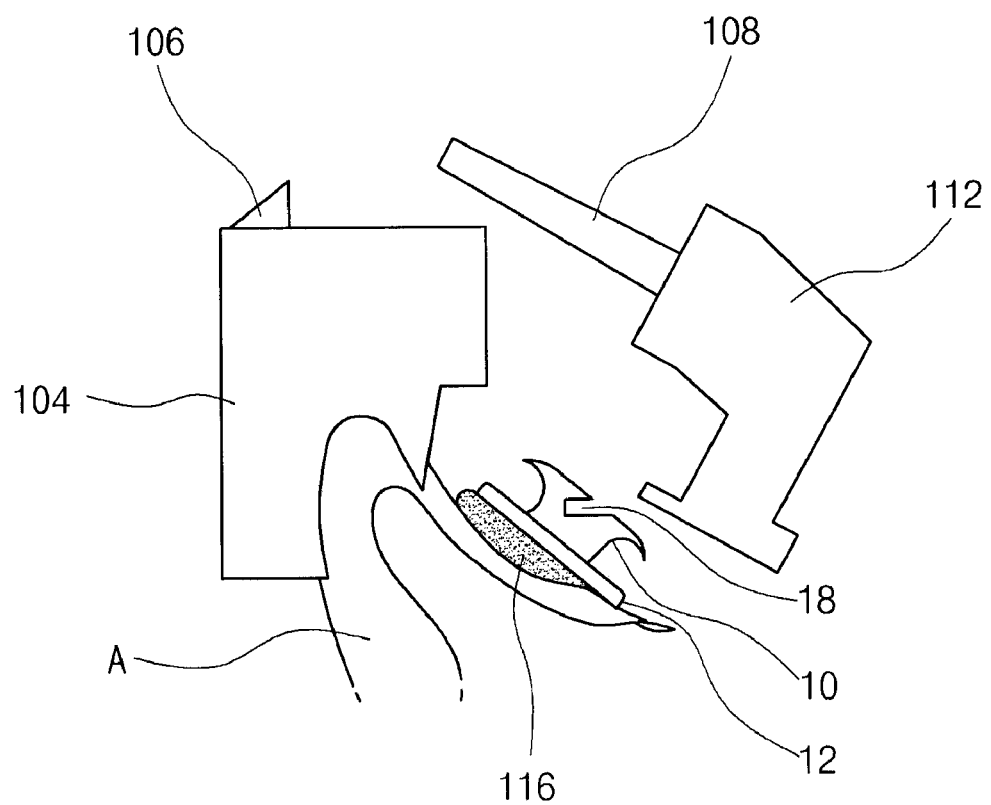

[Figure 12]
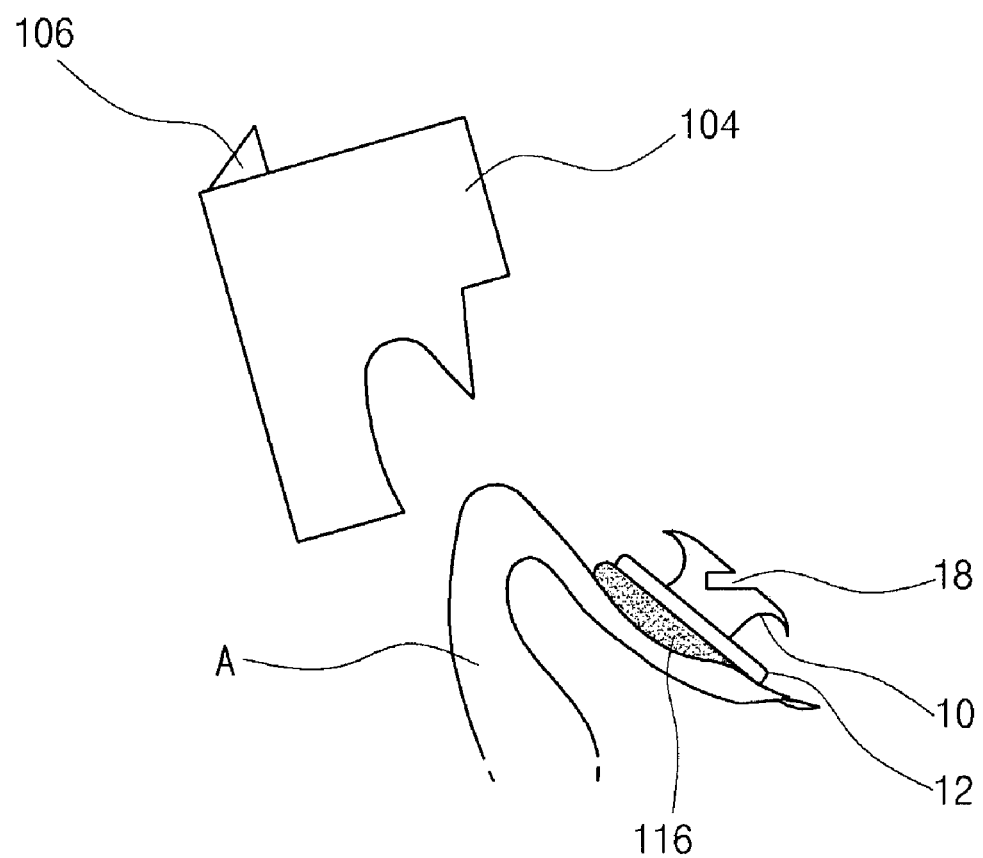

[Figure 13]
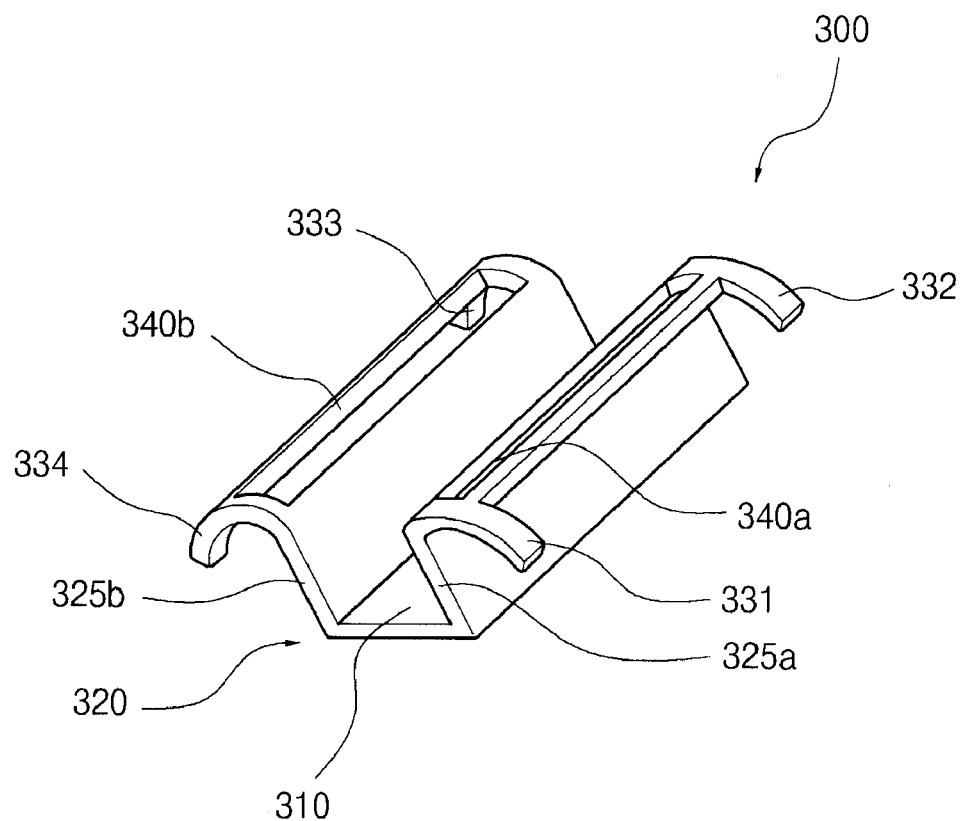

ORTHODONTIC BRACKET, BRACKET POSITIONING JIG, AND SYSTEM FOR REVISING A SET OF TEETH

TECHNICAL FIELD

The present invention relates to a bracket for revising a set of teeth, a bracket positioning jig, a system for revising a set of teeth using the same and a method of making the jig. More particularly, the present invention relates to a bracket for revising a set of teeth, a bracket positioning jig, a system for revising a set of teeth using the same and a method of making the jig, in which an individual prescription value which is the most suitable for an individual patient is applied to the bracket positioning jig in a computer program when the jig is manufactured, and thus even a bracket for revising a set of teeth to which prescription is not given can be used.

BACKGROUND ART

In general, a nonuniform set of tooth or a false occlusion (a bite of tooth does not fit) is caused by cacogenesis of tooth themselves, cacogenesis of jawbones, or bad habits of sucking fingers early in life, with a result that tooth do not grow right in place.

People who have a nonuniform set of tooth or a false occlusion would hide their mouths due to the ugly tooth row when talking or laughing with another person or cope negatively with personal relations. Accordingly, they may not live a smooth social life, respectively. They may not also pulverize food evenly at the time of food intake. Further, food dregs may be caught in gaps between the tooth. As a result, various kinds of cacodontias or disease of the digestive system may be caused.

To solve these conventional problems, continuous force is applied to tooth, to thus medically treat correction of a row of irregular tooth of a principle of bring about a transfer of tooth with reconstruction of alveolar bones which enclose tooth.

A conventional bracket has a characteristic angle known as so-called prescription between a base portion and a groove or slot. The bracket helps treatment easily performed due to an inherent set angle, but the conventional bracket is of an expensive additional production cost including a processing treatment cost for this reason, to thereby cause a price of a product to amount very high.

That is, the bracket for revising a set of teeth according to the conventional art is made using a method of giving an average prescription value with respect to each bracket. That is, it is the best to give a suitable prescription value to individual patients, respectively. However, considerable effort and expense is required to give a suitable prescription value to individual patients, respectively. Thus, it is not so easy in actuality to employ the method of giving an average prescription value with respect to each bracket, to resultantly drop a function of the bracket.

The conventional bracket is manufactured by resin or ceramics and is not seen well due to the fact that the color of the bracket is similar to the color of tooth but causes prices to increase.

Also, brackets become smaller so that a patient does not feel less a sense of a foreign matter but feel comfortable when the brackets are attached to the patient's teeth. However, this also becomes a price rising factor. Further, brackets are required to become products which can be easily installed for patients in a short time.

On the other hand, orthodontics treatment is performed by attaching a bracket for revising a set of teeth on the respective surfaces of the tooth and controlling a wire which is combined into a groove or slot formed in the bracket. To transfer a force of the wire correctly to the bracket at the time of the orthodontics treatment, positioning of the bracket which is attached on the surfaces of the tooth plays a very important part in the orthodontics treatment process and result. Therefore, it is required a tool for reconstructing a position of the bracket designed or planned through diagnostic on the surfaces of the tooth of the patient's exactly.

A tool which exactly holds a bracket's installation position in the patient's teeth is called a bracket positioning jig or transfer jig. Most conventional bracket positioning jigs or transfer jigs have been manufactured by dentists directly or manufactured manually in a workshop. That is, liquefied resin is poured into a bracket-mounted gypsum tooth model and then cured. Then, the gypsum tooth model is removed and the gypsum tooth are cut and elaborated to fit in the respective teeth. Accordingly, a customized jig for the respective teeth is manufactured.

In the following, a conventional orthodontics treatment bracket for revising a set of teeth and a conventional bracket positioning jig will be described with reference to FIGS. 1A and 1B.

As illustrated in FIG. 1A, a general orthodontics treatment bracket 10 for revising a set of teeth has a shape that a pair of wings 14 and 16 which are spaced by a predetermined interval are integrally formed on a base 12 attached on a tooth "A." A slot 18 into which a wire (not shown) is inserted is formed between the wings 14 and 16 is formed.

The orthodontics treatment bracket 10 for revising a set of teeth is attached on the surface of a lip side (that is, an outer side) of the tooth or a tongue side (that is, an inner side). However, the orthodontics treatment bracket 10 is recently attached on the tooth at the tongue side, considering that the orthodontics treatment bracket is exposed externally at the time of personal relations.

Before an orthodontics treatment bracket 10 for revising a set of teeth is mounted on the tooth, the bracket 10 is installed in the lower portion of a jig 30 that is manually manufactured, as illustrated in FIG. 1B.

The jig 30 includes a cap 34 having a receptacle 32 which accommodates a tooth, and a support 38 which is installed at one side of the rear surface of the cap 34, and which has a coupler 36 which combines an orthodontics treatment bracket for revising a set of teeth with the lower portion of a jig body. Here, in the case of the conventional jig, the cap 34 and the support 38 are integrally formed into one body.

A process of using the jig 30 as constructed above will be described as follows.

First, the orthodontics treatment bracket 10 for revising a set of teeth is coupled on the coupler 36 of the jig 30. Then, the orthodontics treatment bracket 10 is placed on the surface of the tooth and the receptacle 32 formed in the cap 34 of the jig 30 is placed on the tooth.

Thereafter, the bracket 10 is fixed on the surface of the tooth by curing thermosetting resin which is attached on the bottom of a base of the orthodontics treatment bracket 10 for revising a set of teeth 10, using laser and the jig 30 is separated from the tooth.

In this case, because the jig 30 has the cap 34 and the support 38 which are integrated into one body, there is a problem that the jig 30 is not easily separated from the tooth.

When the bracket 10 is attached on the surface of the tooth, a user a dentist can mount the bracket 10 correctly and safely as a portion (an area) where the jig 30 contacts the tooth becomes wider. However, since the conventional bracket positioning jig is formed into a single body, the area where the jig 30 contacts the tooth is limited due to a problem which occurs at the time of removal of the jig after the orthodontics treatment bracket has been mounted on the tooth.

In addition, a three-dimensional relationship (that is, angle/distance) of a tooth and a bracket for treatment is called as "prescription." This means a relationship between a wire for treatment and a groove (slot) which is located in the bracket. Therefore, since the jig should express these relationships among the bracket, the wire, and the tooth, but the jig that has been manually manufactured is based on the external shape not a slot of the bracket, accuracy of the jig drops.

In addition, in the case that an orthodontics treatment bracket for revising a set of teeth which has been attached to a patient is detached from the patient, the orthodontics treatment bracket should be attached to the patient again in the conventional technology. However, if the manually manufactured jig has been lost, the lost jig should be newly manufactured again together with a jig for other tooth.

In particular, since a conventional bracket positioning jig is manually manufactured, a production and purchase cost is very high, and quality of the product is also consistent. As a result, such a conventional bracket positioning jig makes a bad influence upon the result of treatment, and should be abolished after use one time.

Further, in the case of the conventional jig, one patient needs about 20-30 jigs. Accordingly, it is very difficult to keep recording of marks for different jigs.

Korea Laid-open Patent Publication No. 2006-20214 discloses "Integral multi-purpose bracket attachment apparatus with indicated height and angle of tooth" but the structure is very complicated and thus there is a problem that a manufacturing cost is high.

In addition, Korea Laid-open Patent Publication No. 2002-16324 discloses "Positioning and attachment auxiliary apparatus for settlement type orthodontics treatment brackets, which includes a molding portion which is coupled with the top end of a tooth, a main body which is extended from the upper portion of the molding portion to the surface of the tooth, and a rubber ring which combines the main body and a bracket. However, since the molding portion and the main body which play an important role of deciding a bracket attachment position are manually manufactured in this technology, it is difficult and complicated to perform a correct positioning work for a bracket, and it is not simple to separate the molding portion and the main body after attachment of the bracket. Further, there is a problem that cost rises because the orthodontics treatment apparatus is manually manufactured.

DISCLOSURE

Technical Problem

To solve the above problems, it is an object of the present invention to provide a system for revising a set of teeth in which an individual prescription value which is the most appropriate for an individual patient is given to a bracket positioning jig on a computer program to thus manufacture a desired jig, and to thereby be capable of using a non-prescription bracket as well as an orthodontics treatment bracket for revising a set of teeth having a given prescription value.

It is another object of the present invention to provide a system for revising a set of teeth in which a teeth set up for revising a set of teeth is performed on a computer program, and then a jig is manufactured using a pre-designed value, so that the orthodontics treatment teeth revising system is mounted on a patient using the jig, with a result that a positioning surgical operation of a bracket for the surfaces of the tooth can be achieved easily and correctly, and bending mold data for a revising wire is used at the time of a teeth set up for revising a set of teeth, to then reflect the bending mold data at the time of operation of bending the revising wire for revising a set of teeth after attachment of the bracket on the tooth.

It is still another object of the present invention to provide a bracket positioning jig for revising a set of teeth in which a cap which is separably combined with a tooth and a connector at the lower end of which a bracket is combined are manufactured in a detachable separable structure, with a result that only the cap contacting the tooth is abandoned and the connector is re-used, to thus reduce a user's burden.

It is yet another object of the present invention to provide a system for revising a set of teeth in which a cap portion contacting a tooth can be separated and freely adjusted, to thereby achieve a maximum contact area for mounting a bracket safely and accurately, and the lower portion of a jig is detachably combined with a groove or slot of the bracket, to thus regenerate a relationship between the bracket and the tooth accurately.

It is yet still another object of the present invention to provide a bracket for revising a set of teeth in which the bracket is manufactured based on a non-prescription method and thus can be manufactured in small size and a very simple structure, to thereby minimize a sense of a foreign matter and make a user feel comfortable even in the case that the bracket is used in a mouth for long and to thus solve a problem of cleaning the mouth and the bracket by food and secretion.

It is a further object of the present invention to provide a bracket positioning jig for revising a set of teeth and a system thereof in which even in the case that a jig is lost, only the lost jig can be re-manufactured using data stored in a computer.

It is another further object of the present invention to provide a bracket positioning jig for revising a set of teeth and a method thereof in which since a cap of a jig is designed and manufactured using a CAD/CAM system, quality of products is consistent and excellent, and mass-produced at a low price.

Technical Solution

To accomplish the above object of the present invention, according to an aspect of the present invention, there is provided a system for revising a set of teeth comprising: a bracket for revising a set of teeth; and a bracket positioning jig for attaching the bracket for revising a set of teeth on the surface of the tooth.

According to an aspect of the present invention, there is provided an orthodontics treatment bracket for revising a set of teeth, the bracket comprising: a base whose lower portion is attached in a tooth; first and second vertical portions which are extended vertically from both side ends of the base to form a slot in which a coupler for a bracket positioning jig or a wire for revising a set of teeth is inserted at the center of the upper surface to lengthy direction; and first through fourth hooks which are ramified from the centers of the first and second vertical portions and bent downwards, respectively.

In the bracket for revising a set of teeth, the first through fourth hooks are modified to be extended from the upper end edges of the first and second vertical portions so as to be bent downwards, respectively. In this case, the orthodontics treatment bracket for revising a set of teeth further comprises a pair of hollow windows for confirming whether or not bonding is performed using a thermosetting bond when the base is attached in a tooth along the lengthy direction of both side upper top portions of the first and second vertical portions.

According to an aspect of the present invention, the bracket for revising a set of teeth is of a non-prescription structure in which the lower portion of the base and the slot are run in parallel.

The bracket positioning jig comprises: a cap at the lower portion of which a groove contacting tooth is formed, and which has a throughhole to lengthy direction on the upper portion of a cap body; and a connector one side of which has a fixed protrusion which is detachably inserted into and fixed to the throughhole of the cap, and the other side of which is bent toward the lower end of the body and has a coupler which is combined on a slot of an orthodontics treatment bracket for revising a set of teeth.

According to an aspect of the present invention, the orthodontics treatment bracket for revising a set of teeth is of a non-prescription type, and the cap is given with a prescription by relevant tooth.

According to an aspect of the present invention, the cap of the bracket positioning jig is designed to apply an individual prescription value which is the most appropriate for an individual patient to the bracket positioning jig, on a computer program, to decide a shape of the groove according to shapes of combined tooth, to then manufacture the bracket positioning jig. Accordingly, the bracket for revising a set of teeth which is given with an average prescription in advance may be used.

According to an aspect of the present invention, there is also provided a system for revising a set of teeth comprising: a non-prescription type bracket for revising a set of teeth having a slot in which a wire for revising a set of teeth is inserted, and runs a base surface in parallel; and a bracket positioning jig which is given with a prescription according to shape and position of tooth to which the bracket for revising a set of teeth is attached on the surface of the tooth.

According to an aspect of the present invention, there is also provided a method of manufacturing a bracket position jig for revising a set of teeth, the method comprising the steps of: obtaining three-dimensional (3D) shape data for patient's teeth by 3D scanning using a 3D scanner for teeth computer modelling after manufacturing a patient's teeth gypsum pattern; performing a teeth set up for a bracket for revising a set of teeth for orthodontics treatment on a computer system in which an orthodontics treatment dedicated program is loaded, after having obtained the 3D teeth shape data; reading image data for the bracket positioning jig which is stored in a storage device of the computer system after having completed the teeth set up, and combining the coupler of the bracket positioning jig onto the slot for the bracket for revising a set of teeth and combining the lower portion of the cap with the tooth; separating digital shape data of the bracket positioning jig in which both the teeth set up and the bracket set up have been reflected; molding only a cap portion with resin by a rapid prototyping (RP) molding machine using digital shape data of the bracket positioning jig; and combining the fixed protrusion of the coupler which has been manufactured in advance in the cap with the throughhole of the cap.

According to an aspect of the present invention, the step of performing the teeth set up for the orthodontics treatment bracket for revising a set of teeth, comprises the steps of: reading the 3D teeth shape data on the computer system in which the teeth revising dedicated program is loaded; combining the bracket for revising a set of teeth with the wire for revising a set of teeth, by attaching the bracket for revising a set of teeth with the respective teeth on the teeth revising dedicated program and making the wire for revising a set of teeth pass through the slot of the bracket for revising a set of teeth; and making the respective teeth manually move to desired revised positions, or rearranging the tooth to form a uniform tooth alignment through an automatic teeth revising function.

According to an aspect of the present invention, in the case that the coupler for the bracket positioning jig is combined with the slot of the bracket for revising a set of teeth, and the lower portion of the cap is combined with the tooth, the teeth shape data is invariable and the cap portion is combined with the tooth in a manner that a portion which overlaps the tooth is removed, and wherein in the case that the digital shape data of the bracket positioning jig is separated, the patient's teeth traces are formed on the bottom of the cap of the separated bracket positioning jig.

The present invention can obtain an excellent treatment result by applying an individual prescription value which is the most appropriate for an individual patient to the bracket positioning jig, on a computer program, instead of an average prescription value which is possessed by a general bracket.

Advantageous Effects

As described above, the present invention provides a system for revising a set of teeth in which an individual prescription value which is the most appropriate for an individual patient is given to a bracket positioning jig on a computer program to thus manufacture a desired jig, and to thereby be capable of using a non-prescription bracket as well as an orthodontics treatment bracket for revising a set of teeth having a given prescription value. As a result, the bracket is manufactured based on a non-prescription method and thus can be manufactured in small size and a very simple structure, to thereby minimize a sense of a foreign matter and make a user feel comfortable even in the case that the bracket is used in a mouth for long.

In addition, the present invention provides a system for revising a set of teeth in which a teeth set up for revising a set of teeth is performed on a computer program, and then a jig is manufactured using a pre-designed value, so that the orthodontics treatment teeth revising system is mounted on a patient using the jig, with a result that a positioning surgical operation of a bracket for the surfaces of the tooth can be achieved easily and correctly, and bending mold data for a revising wire is used at the time of a teeth set up for revising a set of teeth, to then reflect the bending mold data at the time of operation of bending the revising wire for revising a set of teeth after attachment of the bracket on the tooth.

In addition, the present invention provides the bracket manufactured in a very simple structure, based on a non-prescription method to thus easily solve a problem of cleaning the mouth and the bracket by food and secretion, and provides the bracket which is cheaper at a price less than one tenth in comparison with the conventional product to thus provide an excellent product competition.

In the present invention, since the bracket is mounted onto a patient using a jig having a value that is designed on a computer as it is, a bracket positioning surgical operation for the surfaces of the tooth can be quickly and easily performed by a general dentist as well as a teeth revising specialist. As a result, surgical operation time is greatly shortened because the bracket surgical operation is easily achieved.

In the bracket positioning jig for revising a set of teeth according to the present invention, a cap which is separably combined with a tooth and a connector at the lower end of which a bracket is combined are manufactured in a detachable separable structure, and size of the bracket is small in size and simple in structure. Accordingly, it is possible to perform a surgical operation of the jig at the tongue or lip side of the tooth.

In the present invention, a cap portion contacting a tooth can be separated and freely adjusted, to thereby achieve a maximum contact area for mounting a bracket safely and accurately, and the lower portion of a jig is detachably combined with a groove or slot of the bracket, to thus regenerate a relationship between the bracket and the tooth accurately. Accordingly, a teeth revising process can be performed quickly and accurately.

Further, even in the case that a jig is lost in the present invention, only the lost jig can be re-manufactured using data stored in a computer. In addition, since a cap of a jig is designed and manufactured using a CAD/CAM system, quality of products is consistent and excellent, and mass-produced at a low price.

In addition, the jig is divided into two portions of the cap portion and the connector portion, with a result that only the cap contacting the tooth is abandoned and the connector is re-used, to thus reduce a user's burden. If a dentist scans only laser onto a thermosetting bond and cures the thermosetting bond at the state where the cap portion is made to contact the tooth, bracket position and fixing is completed. As a result, surgical operation time is greatly shortened in comparison with the conventional art.

DESCRIPTION OF DRAWINGS

The above and/or other objects and/or advantages of the present invention will become more apparent by describing the preferred embodiments thereof in detail with reference to the accompanying drawings in which:

FIG. 1A is a perspective view showing a general bracket for revising a set of teeth;

FIG. 1B is a perspective view showing a jig for a bracket for revising a set of teeth according to the conventional art;

FIG. 2 is a perspective view showing a bracket positioning jig of a bracket for revising a set of teeth according to the present invention;

FIG. 3 is a perspective view showing the state where a cap and a connector of FIG. 2 are detached from each other;

FIG. 4A is a perspective view showing a bracket f or revising a set of teeth according to a first exemplary embodiment of the present invention;

FIG. 4B is a vertical cross-sectional view showing the bracket for revising a set of teeth along a line X-X' of FIG. 4A;

FIG. 4C is a horizontal cross-sectional view showing the bracket for revising a set of teeth according to the present invention;

FIG. 5 is a perspective view showing three-dimensional (3D) shape data for patient's teeth which are read on a teeth revising dedicated program;

FIG. 6 is a perspective view for explaining a process of performing a tooth setting operation for orthodontics treatment using a teeth revising dedicated program after having obtained the 3D teeth shape data;

FIG. 7 is a perspective view for explaining the state of combining the bracket positioning jig for bracket attachment with the bracket using the teeth revising dedicated program after having completed the tooth setting operation;

FIG. 8 is a perspective view showing the state where the respective bracket positioning jigs are separated using a Boolean function on the teeth revising dedicated program;

FIG. 9 is a perspective view showing the state where a prefabricated connector is combined after the connector is prefabricated using resin in a rapid prototyping (RP) molding machine using shape data for cap portion of the bracket positioning jig which has been obtained from FIG. 8;

FIG. 10 is a perspective view for explaining a process of combining a teeth revising bracket with the bracket positioning jig manufactured according to the present invention and automatically positioning a bracket onto the surface of the tooth;

FIGS. 11 and 12 are perspective views showing a process of separating the bracket positioning jig according to the present invention from the tooth; and FIG. 13 is a perspective view showing a bracket for revising a set of teeth according to a second exemplary embodiment of the present invention.

Best Mode

Hereinbelow, a system for revising a set of teeth and a method of manufacturing the same according to preferred embodiments of the present invention will be described with reference to the accompanying drawings. Like reference numerals denote like elements through the following embodiments.

FIG. 2 is a perspective view showing a bracket positioning jig of a bracket for revising a set of teeth according to the present invention, and FIG. 3 is a perspective view showing the state where a cap and a connector of FIG. 2 are detached from each other.

As illustrated in FIGS. 2 and 3, a jig 100 for a bracket for revising a set of teeth according to the present invention includes a cap 104 whose lower portion contacts and is combined with the upper portion of a tooth and which is formed into a substantially rectangular box shape having a throughhole 102 in lengthy direction along the inside of the upper portion of a cap body and a triangular protrusion 106 which is installed in the central end of the upper surface of the cap body so as to be caught by one end of a separation device (not shown); and an "L"-shaped connector 112 at one side of which a fixed protrusion 108 which is inserted into and fixed to the throughhole 102 formed in the cap 104 is formed and which has a coupler 110 which are extended inwards and outwards so that a teeth revising bracket (not shown) is combined on the lower end of the connector 112 which is bent downwards and extended from the cap body.

Preferably, the throughhole 102 is of a tapered shape in which width of the throughhole 102 becomes smaller as it goes from entrance of the throughhole 102 with which the fixed protrusion 108 is combined to exit thereof. Likewise, the fixed protrusion 108 of the connector 112 is of a tapered shape in which width of the fixed protrusion 108 becomes smaller as it goes to the leading end thereof, so as to correspond to the inner structure of the throughhole 102. In this case, the throughhole 102 and the fixed protrusion 108 have been illustrated to form a rectangular shape, respectively, but they may be formed into other shapes such as a circular shape in their sectional shapes. A certain geometry that the fixed protrusion 108 is pressed into and combined with the throughhole 102 can be also available. It is preferable that the fixed protrusion 108 is formed a little longer that than lengthy of the throughhole 102.

The protrusion 106 is integrally formed in the cap 104. As will be described later, the bracket is fixed on a tooth of a patient using the jig 100. Thereafter, when the jig is removed, the fixed protrusion 108 of the connector 112 which is projected to one side of the cap 104 is depressed using a tool such as tongs. Accordingly, the connector 112 is separated from the cap 104, according to the press of the fixed protrusion 108. In this case, the protrusion 106 acts as a support. Thus, any shape of the protrusion 106 may be applied if it is a structure of playing a role of a support.

The connector 112 includes a pair of wing 114a and 114b at the rear end of the fixed protrusion 108, to act as a stopper when the fixed protrusion 108 is combined in the throughhole 102.

FIG. 4A is a perspective view showing a bracket f or revising a set of teeth according to a first exemplary embodiment of the present invention. FIG. 4B is a vertical cross-sectional view showing the bracket for revising a set of teeth along a line X-X' of FIG. 4A. FIG. 4C is a horizontal cross-sectional view showing the bracket for revising a set of teeth according to the present invention.

As illustrated in FIGS. 4A, 4B and 4C, an orthodontics treatment bracket 200 for revising a set of teeth, includes: a base 220 whose lower portion is attached in a tooth (not shown); first and second vertical portions 225a and 225b which are extended vertically from both side ends of the base 220 to form a slot 210 that a coupler 110 for a bracket positioning jig 100 or a wire 11 of FIG. 7 for revising a set of teeth is inserted at the center of the upper surface to lengthy direction; and first through fourth hooks 230 which are ramified from the centers of the first and second vertical portions 225a and 225b and bent downwards, respectively.

The first through fourth hooks 230 are used to hang up an elasticity band etc., to inflict a force to a tooth in a particular direction, at the state where they are attached to the surface of the tooth.

Spaces which are formed between two respectively adjacent hooks among the first through fourth hooks 230 play a role of a pair of hollow windows 240 for confirming whether or not bonding is performed using a thermosetting bond when the base 220 is attached in a tooth.

The lower portion of the base 220 and the slot 210 are run in parallel. Any prescription is not given between the base 220 and the slot 210.

The bracket 200 according to the first exemplary embodiment is made of for example, medical stainless steel. Since prescription is given for a jig, prescription need not be given for a bracket. Accordingly, the bracket may be fabricated in a very simplified shape and simple manner and in small size.

A design simulation of the bracket for revising a set of teeth and the bracket positioning jig using the same and an actual surgical operation process according to the present invention having the above-described structures, will be described with reference to FIGS. 5 through 12.

In a system for revising a set of teeth according to the present invention, an individual prescription value which is the most appropriate for an individual patient is given to a bracket positioning jig on a computer program to thus manufacture a desired jig, and to thereby be capable of using a non-prescription bracket of FIG. 4A as well as an orthodontics treatment bracket for revising a set of teeth having a given prescription value of FIG. 1A.

On the following description according to the exemplary embodiments, a non-prescription bracket 200 will be described with reference to of FIGS. 6 and 7, and a bracket 10 assigned with a predetermined prescription value will be described with reference to of FIGS. 10 through 12.

First, after manufacturing a patient's teeth gypsum pattern by a dentist, three-dimensional (3D) shape data for patient's teeth by 3D scanning using a 3D scanner (not shown) for teeth computer modelling is extracted as shown in FIG. 5. FIG. 5 is a perspective view showing three-dimensional (3D) shape data for patient's teeth which are read on a teeth revising dedicated program.

Thereafter, the dentist can set up a position of a bracket on a computer system, using a teeth set up dedicated program which enables the dentist to predict a result after the teeth revising orthodontics treatment with the obtained teeth shape data, that is, 3D teeth CAD data. Using the teeth set up dedicated program, it is possible to design a prediction/treatment apparatus for predicting a diagnosis/treatment result and treating teeth revising treatment according to the diagnosis/treatment result.

FIG. 6 is a perspective view for explaining a process of performing a tooth setting operation for orthodontics treatment using a teeth revising dedicated program after having obtained the 3D teeth shape data.

A dentist reads the 3D teeth CAD data on the computer system in which the teeth revising dedicated program is loaded. The read 3D teeth CAD data is data that can move respective teeth "A" one by one. Then, the bracket 200 is attached to the respective teeth "A" and the wire 11 for revising a set of teeth is made to pass through the slot 210 of the bracket 200, and thus the bracket 200 is combined with the wire 11. Then, the respective teeth "A" manually move to desired revised positions, or are rearranged to form a uniform tooth alignment through an automatic teeth revising function. If this teeth set up for teeth revising is achieved, a bent portion 13 is formed along the revising wire 11. After brackets are attached to teeth at later time, this data is reflected on a surgical operation for teeth revising.

FIG. 7 is a perspective view for explaining the state of combining the bracket positioning jig for bracket attachment with the bracket using the teeth revising dedicated program after having completed the tooth setting operation.

If the teeth set up is ended as described above, image data for the bracket positioning jig 100 which is prefabricated for each bracket 200, and stored in a storage device as shown in FIG. 7, and the coupler 110 of the bracket positioning jig is combined onto the slot 210 for the bracket 200. Thus, the shape data of the teeth "A" is invariable and the cap portion 104 is combined with the tooth "A" in a manner that a portion which overlaps the tooth "A" is removed.

As a result, the lower portion of the cap portion 104 combined with the tooth "A" of the bracket positioning jig 100 has a different shape according to the shape of the upper portion of a tooth and the attachment position of the bracket 200.

FIG. 8 is a perspective view showing the state where the respective bracket positioning jigs are separated using a Boolean function on the teeth revising dedicated program.

As shown in FIG. 8, respective bracket positioning jigs are separated using a Boolean function to obtain shape data of the bracket positioning jig 100, at the state where the bracket positioning jig is combined with the bracket using the teeth revising dedicated program. Patient's teeth traces "B" are formed on the bottom of the cap 104 of the separated bracket positioning jig 100. As a result, shape data of a patient customized bracket positioning jig 100 is obtained.

Final data of the bracket positioning jig 100 illustrated in FIG. 8 is digital shape data into which the both the teeth set up and the bracket set up are reflected. The final digital shape data of the bracket positioning jig 100 is transferred to a fabrication shop or workshop which possesses a rapid prototyping (RP) molding machine. Accordingly, the RP molding machine manufactures only a cap 104 of the bracket positioning jig 100 with transparent resin. The digital shape data is supplied to the RP molding machine after conversion has been achieved into a CAD file so that a CAM work may be available in the present invention.

In the present invention, because all necessary prescriptions for revising a set of teeth are reflected for the cap 104 of the bracket positioning jig 100, the connector 112 the cap 104 and the bracket 200 combined with the connector 112 may not change in shape according to a patient or teeth. As a result, the connector 112 and the bracket 200 can be mass produced in advance to thus lower a manufacturing cost, in the present invention. In addition, because these parts can be re-used after cleaning or washing, a user can greatly reduce a burden of expenses to be consumed in an orthodontics surgical operation. The connector 112 is manufactured into three kinds in size of the tooth which are classified into a front tooth, a denticle and a molar tooth.

Thereafter, the cap 104 of the jig 100 is combined with the connector 112, as illustrated in FIG. 9.

Thereafter, as illustrated in FIG. 10, if the cap 104 of the jig 100 is safely loaded on the upper portion of the tooth "A," after having combined the coupler 110 of the jig 100 with the slot of the bracket 10 for revising a set of teeth, the base 12 of the bracket 200 for revising a set of teeth is established in a predetermined position on the surface of the tooth.

Then, the bracket 10 is fixed to the tooth "A" by curing thermosetting bond 116 which is attached on the bottom of the base 12 by laser in advance.

If the curing procedure is ended, the fixed protrusion 108 of the connector 112 that is projected from the throughhole 102 of the cap 104 is pressed using a separation tool. Accordingly, as illustrated in FIG. 11, the fixed protrusion 108 is pushed out in the throughhole 102 of the cap 104, and simultaneously the connector 112 is detached from the cap 104 and the bracket 10.

Then, the cap 104 of the jig 100 is separated from the tooth "A" as illustrated in FIG. 12.

Then, the revising wire (not shown) is inserted into the slot 18 of the bracket 10, and the revising wire is bent as shown in FIG. 6, to thereby introduce displacement of a desired direction in the bracket 10 for revising a set of teeth.

As described above, the present invention enables a user to use any kind of even a bracket given with prescription together with a bracket positioning jig. Further, in the present invention, because prescription is given for a bracket positioning jig, it is possible to use a type of a product having no prescription as a bracket.

Moreover, as described above, a non-prescription bracket 200 has been described with reference to of FIGS. 6 and 7, and a bracket 10 assigned with a predetermined prescription value has been described with reference to of FIGS. 10 through 12. However, the same bracket model as that used when the prescription is given to the bracket positioning jig 100 on the dedicated program should be used when the bracket is attached to the tooth.

FIG. 13 is a perspective view showing a bracket for revising a set of teeth according to a second exemplary embodiment of the present invention. The bracket 300 of FIG. 13 is similar to the structure of the first embodiment of the present invention. The bracket 300 of FIG. 13 includes: a base 320 whose lower portion is attached in a tooth (not shown); first and second vertical portions 325a and 325b which are extended vertically from both side ends of the base 320 to form a slot 310 in which a coupler 110 for a bracket positioning jig 100 or a wire (not shown but depicted as 11 in FIG. 7) for revising a set of teeth is inserted at the center of the upper surface to lengthy direction; first through fourth hooks 331 through 334 which are ramified from the upper end edges of the first and second vertical portions 325a and 325b and are extended so as to be bent downwards, respectively; and a pair of hollow windows 340a and 340b for confirming whether or not bonding is performed using a thermosetting bond when the base 320 is attached in a tooth along the lengthy direction of both side upper top portions of the first and second vertical portions 325a and 325b.

The first through fourth hooks 331 through 334 are used to hang up an elasticity band etc., to inflict a force to a tooth in a particular direction, at the state where they are attached to the surface of the tooth.

The lower portion of the base 320 and the slot 310 are run in parallel, and prescription is not given between the base 320 and the slot 310.

The bracket 300 according to the second exemplary embodiment is made of for example, medical stainless steel. Since prescription is given for a jig, prescription need not be given for a bracket. Accordingly, the bracket may be fabricated in a very simplified shape and simple manner and in small size.

Mode For Invention

As described above, the present invention has been described with respect to particularly preferred embodiments. However, the present invention is not limited to the above embodiments, and it is possible for one who has an ordinary skill in the art to make various modifications and variations, without departing off the spirit of the present invention. Thus, the protective scope of the present invention is not defined within the detailed description thereof but is defined by the claims to be described later and the technical spirit of the present invention.

INDUSTRIAL APPLICABILITY

As described above, the present invention is applied to a system for revising a set of teeth including a bracket for revising a set of teeth and a bracket positioning jig to perform an orthodontics treatment for teeth revising, to thereby achieve a teeth surgical operation at a low cost and within a short time.

The invention claimed is:

1. A bracket positioning jig for positioning an orthodontics treatment bracket used in revising a set of teeth, the bracket positioning jig comprising:
  a cap having a lower portion contoured to mate with a tooth and position an orthodontics treatment bracket, the cap having a throughhole formed in an upper portion thereof and extending longitudinally therethrough; and
  a connector having a fixed protrusion extending longitudinally from a base portion on one side thereof for detachable insert coupling within the throughhole of the cap, the connector having a pair of wings disposed at the base portion and respectively extending oppositely in a direction transverse to the longitudinal extension of the fixed protrusion to limit a depth of insertion into the throughhole of the cap, another side of the connector being bent toward the lower end of the cap and having a coupler formed thereon for engagement with a slot of an orthodontics treatment bracket used for revising a set of teeth.

2. The bracket positioning jig according to claim 1, wherein the throughhole has a tapered shape from an entrance of the throughhole to an exit thereof, and the fixed protrusion has a taper corresponding to the taper of the throughhole.

3. The bracket positioning jig according to claim 1, wherein a length of the fixed protrusion is greater than a length of the throughhole and thereby providing a portion of the fixed protrusion extending from a distal open end of the throughhole for providing a depressible projection to facilitate removal of the connector from the cap.

4. A system for revising a set of teeth, comprising:
an orthodontics treatment bracket for revising a set of teeth having a slot formed therein; and
a bracket positioning jig for attaching the orthodontics treatment bracket on the surface of a tooth, wherein the bracket positioning jig comprises:
a cap having a lower portion contoured to mate with a tooth and position the orthodontics treatment bracket, the cap having a throughhole formed in an upper portion thereof and extending longitudinally therethrough; and
a connector having a fixed protrusion extending longitudinally from a base portion on one side thereof for detachable insert coupling within the throughhole of the cap, the connector having a pair of wings disposed at the base portion and respectively extending oppositely in a direction transverse to the longitudinal extension of the fixed protrusion to limit a depth of insertion into the throughhole of the cap, another side of the connector being bent toward the lower end of the cap and having a coupler formed thereon for engagement with the slot of the orthodontics treatment bracket.

5. The system for revising a set of teeth according to claim 4, wherein the orthodontics treatment bracket comprises:
a base having a lower portion for attachment to a tooth;
first and second vertical portions respectively extending from two sides of the base to form the slot therebetween; and
a pair of hooks which are ramified from a center of each of the fist and second vertical portions, each of the hooks being bent downwardly.

6. The system for revising a set of teeth according to claim 4, wherein the orthodontics treatment bracket comprises:
a base having a lower portion for attachment to a tooth;
first and second vertical portions respectively extending from two sides of the base to form the slot therebetween, each of the vertical portions having an outwardly bent portion and a slotted opening formed therein to provide an access to confirm bonding of the base to a tooth; and
a pair of hooks extending from the bent portion of each of the fist and second vertical portions, each of the hooks being bent downwardly.

7. The bracket positioning jig according to claim 4, wherein a length of the fixed protrusion is greater than a length of the throughhole and thereby providing a portion of the fixed protrusion extending from a distal open end of the throughhole for providing a depressible projection to facilitate removal of the connector from the cap.

* * * * *